United States Patent [19]

Bosies et al.

[11] 4,376,731

[45] Mar. 15, 1983

[54] 1-AZIRIDINE CARBOXYLIC ACID DERIVATIVES WITH IMMUNOSTIMULANT ACTIVITY

[75] Inventors: Elmar Bosies, Heppenheim; Ruth Heerdt, Mannheim-Feudenheim; Rudi Gall, Hirschberg-Grosssachsen; Uwe Bicker, Mannheim; Anna E. Ziegler, Mannheim-Wallstadt, all of Fed. Rep. of Germany

[73] Assignee: Boehringer Mannheim GmbH, Mannheim, Fed. Rep. of Germany

[21] Appl. No.: 859,633

[22] Filed: Jan. 31, 1978

[51] Int. Cl.³ ............... C07D 203/20; C07D 403/12; C07D 405/12; A61K 31/395
[52] U.S. Cl. ............... 260/239 E; 260/330.3; 260/330.9; 548/465; 424/244; 424/274; 424/275; 424/278
[58] Field of Search ........... 260/239 E, 326 N, 330.3, 260/347.4; 424/244

[56] References Cited

FOREIGN PATENT DOCUMENTS 2644820  4/1978  Fed. Rep. of Germany ... 360/239 E

OTHER PUBLICATIONS

Osterreichische Zeitschrift für Onkologie 1977, vol. 1, pp. 29–31.
Micksche et al., *Austrian Journal of Oncology*, vol. 4, 29–32, (1977).
"Burgers Medicinal Chemistry", 4th Edition, Part II, pp. 694–699, (1979).
Lwowski et al., TET Letters 1964, 2497.
Bernstein et al., Tetrahedron 1977, 33, pp. 881–883, (Apr. 1977).

*Primary Examiner*—Mark L. Berch
*Attorney, Agent, or Firm*—Sprung, Horn, Kramer & Woods

[57] ABSTRACT

2-Substituted-1-aziridine-carboxylic acid esters exhibiting immuno-stimulant activity and of the formula

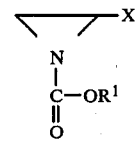

wherein
X is a carbamoyl or alkoxycarbonyl radical, and
$R^1$ is an aliphatic hydrocarbon radical optionally substituted by halogen, alkoxy, amino, carbamoyloxy, cycloalkyl, hydroxyl, an imido or heterocyclic radical, cycloalkyl; or aryl, aralkyl, aryloxyalkyl or arylthioalkyl wherein the aryl moiety is optionally substituted by halogen, alkyl, alkoxy, hydroxyl, amino, nitro, cyano, acyl, carbalkoxy, thioalkyl, alkylsulphonyl, phenyl or trifluoromethyl. Counterparts where X is —CN and $R^1$ is as above, except for ethyl, are also new.

8 Claims, No Drawings

1-AZIRIDINE CARBOXYLIC ACID DERIVATIVES WITH IMMUNOSTIMULANT ACTIVITY

The present invention is concerned with the preparation of 1-aziridine-carboxylic acid ester derivatives, some of which are new.

In Tetrahedron Letters, 1964, 2497, Lwowski et al. have described ethyl 2-cyano-1-aziridine-carboxylate, as well as processes for the preparation thereof but without giving any indication of its pharmacological action. In the course of investigations concerning 2-cyano-1-aziridine-carboxamide, which is an immune-stimulating therapeutic compound in cases of bacterial and viral infections (see German Patent Application No. 25 28 460.0), we found that ethyl 2-cyano-1-aziridine-carboxylate can be used as an intermediate for the preparation of this therapeutic compound.

Furthermore, we surprisingly also found that ethyl 2-cyano-1-aziridine-carboxylate displays an outstanding immune-stimulating action. Therefore, we have further investigated this type of compound, as well as processes for the preparation of the known and new compounds.

Thus, the present invention is concerned with the preparation of compounds of the general formula:

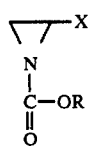

(I)

in which X is a nitrile, carbamoyl or alkoxycarbonyl radical, R is a straight or branched-chain, saturated or unsaturated aliphatic hydrocarbon radical, which can be substituted by halogen, alkoxy, amino, carbamoyloxy, cycloalkyl, hydroxyl or imido groups or by a heterocyclic radical, or R is a cycloalkyl, aryl, aralkyl, aryloxyalkyl or arylthioalkyl radical, the aryl radical being optionally substituted by halogen, alkyl, alkoxy, hydroxyl, amino, nitro, cyano, acyl, carbalkoxy, thioalkyl, alkylsulphonyl, phenyl or trifluoromethyl groups.

The present invention is also concerned with pharmaceutical compositions with an immune-stimulating action which contain these compounds.

The aliphatic hydrocarbon and alkyl radicals are, in all cases, to be understood to be straight or branched-chained radicals containing up to 5 carbon atoms, the preferred radicals being the methyl, ethyl, isobutyl, sec.-butyl, tert.-butyl and n-pentyl radicals. The alkyl or aliphatic hydrocarbon chain can be substituted by halogen atoms, such as fluorine, chlorine and/or bromine atoms, as well as by amino or hydroxyl groups. Further substituents which can be present therein include carbamoyloxy radicals, preferably the 2-cyano-1-aziridine-carbonyloxy radicals, imido groups, for example phthalimido radicals, heterocyclic radicals, especially 2-tetrahydrofuryl or 2-tetrahydrothienyl radicals, and alkoxy and cycloalkyl radicals. In the case of substituents X and R, the alkoxy radical is, in all cases, to be understood to be a radical containing up to 5 carbon atoms, the methoxy, ethoxy and isopropoxy radicals being preferred. The cycloalkyl radicals contain 3 to 10 carbon atoms, the cyclopropyl, cyclopentyl, cyclohexyl radicals being preferred, as well as bridged cycloalkyl radicals, for example bornyl radicals. Preferred unsaturated aliphatic hydrocarbon radicals include the allyl and crotyl radicals.

The aryl radicals are preferably those containing 6 to 10 carbon atoms, especially the phenyl and naphthyl radicals.

The aralkyl radicals are preferably the benzyl or phenethyl radicals, the aryloxyalkyl radical is preferably a 2-phenoxyethyl radical and the arylthioalkyl radical is preferably a 2-phenylthioethyl radical.

The thioalkyl radical is preferably the methylthio radical and the alkylsulphonyl radical is preferably the methylsulphonyl radical. The acyl radical is preferably a formyl or acetyl radical. The halogen atom is to be understood to be a fluorine, chlorine or bromine atom. In all cases, the aryl radical can be substituted one or more times by the above-mentioned substituents.

The present invention also includes within its scope all stereoisomeric forms of the compounds of general formula (I) which can be obtained due to the presence of asymmetrical carbon atoms.

The present invention also provides new compounds of the general formula:

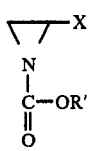

(I')

wherein X has the same meaning as above and R' has the same meaning as R in general formula (I) but with the proviso that when X is a nitrile group, R' is other than an ethyl radical.

As already mentioned above, the compounds of general formula (I) possess, surprisingly, an outstanding immune-stimulating action. Furthermore, when X is a nitrile group, they are valuable intermediates for the preparation of 2-cyano-1-aziridine-carboxamide. For this purpose, compounds of general formula (I), wherein X is a nitrile group, are reacted with ammonia to give 2-cyano-1-aziridine-carboxamide.

The compounds of general formula (I) can be prepared by one of the following processes:

(a) reaction of an aziridine derivative of the general formula:

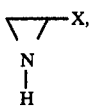

(II)

wherein X has the same meaning as above, with a haloformic acid ester of the general formula:

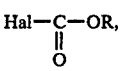

(III)

wherein R has the same meaning as above and Hal is a chlorine or bromine atom; or (b) treatment of a compound of the general formula:

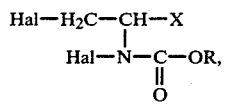

(IV)

wherein X, R and Hal have the same meanings as above, with a reagent splitting off halogen; or (c) conversion of a compound of the general formula:

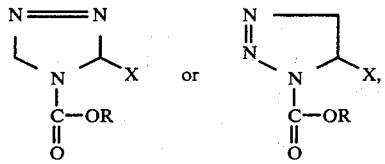

(V)

wherein X and R have the same meanings as above, by the catalytic or photochemical splitting off of nitrogen, to give a compound of general formula (I); whereafter, if desired, a compound obtained of general formula (I) is converted into another compound of general formula (I).

The subsequent conversion of compounds of general formula (I) into other compounds of general formula (I) can, for example, take place by conversion of the substituent X. Thus, for example, when X is an alkoxycarbonyl radical, it can be reacted with ammonia to give a compound in which X is a carbamoyl radical which, in turn, can be treated with a dehydration agent to give a compound in which X is a nitrile group.

Compounds of general formula (I) in which X is an alkoxycarbonyl or carbamoyl group can, therefore, also be used as intermediates for the preparation of compounds of general formula (I) in which X is a nitrile group, this applying particularly to 2-carbamoyl-1-aziridine-carboxylic acid esters of general formula (I).

The conversion of an ester or amide group can best be carried out with gaseous ammonia in an organic solvent, preferably in methanol or ethanol. It is preferable to use equimolar amounts of ammonia and to carry out the reaction at a temperature of 0° to 5° C. The desired amide can then be isolated from the reaction mixture by, for example, column chromatography.

For the conversion of a carbamoyl group into a nitrile group, there can be used dehydration agents which are known for this purpose from the literature, a mixture of triphenyl phosphine, carbon tetrachloride and triethylamine being especially preferred. As solvent, it is usual to employ a halogenated hydrocarbon, for example, methylene chloride or chloroform. The desired nitrile is, as a rule, isolated from the reaction mixture by distillation.

On the other hand, for example, the substituents R and R' can be converted from one to another by generally known methods of esterification: in general, a small addition of a basic substance, for example of an alkali metal or alkaline earth metal hydroxide or of an alkali metal alcoholate, is necessary.

In addition, the new compounds of general formula (I') can be prepared by the reaction of nitrenes of the general formula:

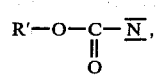

(VI)

wherein R' has the same meaning as above, with compounds of the general formula:

$$CH_2=CH-X$$ (VII), wherein X has the same meaning as above.

Nitrenes of general formula (VI), which can be intermediately prepared by the photolysis of azidoformic acid esters or by α-elimination with the help of bases, such as triethylamine, from N-p-nitrobenzenesulphonyloxyurethanes, readily react with the acrylic acid derivatives (VII) to give the desired aziridines of general formula (I') (see, for example, Tetrahedron Letters, 1964, 2497; J.A.C.S., 87, 3630/1965).

In the case of process (a), the reaction components can be reacted in an inert solvent, for example, diethyl ether, methylene chloride, benzene or toluene, in the presence of a base. The base used is preferably, for example, a tertiary amine, such as triethylamine or triethanolamine. However, it is also possible to work in a two-phase system, such as water/diethyl ether, in which case inorganic bases, especially sodium carbonate, are preferably used. As a rule, the chloroformic acid esters are used as haloformic acid esters. Some of these have already been described in the literature but otherwise they can be prepared in known manner by the reaction of appropriate alcohols or phenols with phosgene in the presence of a base, such as pyridine or N,N-dimethylaniline. As a rule, the chloroformic acid esters are purified by distillation but can possibly also be further reacted as crude products.

The dihalo compounds used in process (b) are new and can be prepared by the reaction of appropriate compounds which are not halogenated on the nitrogen atom with halogenation agents, such as sodium hypohalites or tert.-butyl hypochlorite. For splitting off the two halogen atoms to give the aziridine derivatives of general formula (I), there can be used conventional dehalogenation agents, preferably zinc or sodium.

The triazoline derivatives used in process (c) are also new and can be prepared by the reaction of diazoacetic acid derivatives, such as ethyl diazoacetate or diazoacetonitrile, with methyleneurethanes. The nitrogen can be split off either by illumination in a solvent, such as diethyl ether or acetone, or catalytically. As catalysts, there can be used, for example, noble or seminoble metals, preferably copper powder.

For the preparation of pharmaceutical compositions with immune-stimulating action, the compounds of general formula (I) are mixed in known manner with an appropriate solid or liquid pharmaceutical carrier or diluent and formed, for example, into tablets or dragees or, with the addition of appropriate adjuvants, suspended or dissolved in water or in an oil, such as olive oil, and filled into gelatine capsules. Since the active material is acid-labile, the composition is provided with a coating which only dissolves in the alkaline medium of the small intestines or is admixed with an appropriate carrier material, for example a high molecular weight fatty acid or carboxymethylcellulose. Solid carrier materials which can be used include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavoring and sweetening agents.

As injection medium, it is preferred to use water which contains the additives usual for injection solutions, such as stabilizing agents, solubilizing agents or weakly alkaline buffers. Additives of this type include, for example, phosphate and carbonate buffers, ethanol, complex formers (such as ethylenediamine-tetraacetic acid and the non-toxic salts thereof) and high molecular weight polymers (such as liquid polyethylene oxides) for viscosity regulation.

Preferred compounds according to the present invention include not only those specifically mentioned in the following examples but also the following compounds:
1-chloroethyl 2-cyano-1-aziridine-carboxylate,
1,2-dichloroethyl 2-cyano-1-aziridine-carboxylate,
1,2,2,2-tetrachloroethyl 2-cyano-1-aziridine-carboxylate,
2-methylphenyl 2-cyano-1-aziridine-carboxylate,
2-methoxyphenyl 2-cyano-1-aziridine-carboxylate,
2-chlorophenyl 2-cyano-1-aziridine-carboxylate,
3-chlorophenyl 2-cyano-1-aziridine-carboxylate,
2,4,6-tribromophenyl 2-cyano-1-aziridine-carboxylate,
2-nitrophenyl 2-cyano-1-aziridine-carboxylate,
2-aminophenyl 2-cyano-1-aziridine-carboxylate,
3-aminophenyl 2-cyano-1-aziridine-carboxylate,
4-aminophenyl 2-cyano-1-aziridine-carboxylate,
2-hydroxyphenyl 2-cyano-1-aziridine-carboxylate,
4-hydroxyphenyl 2-cyano-1-aziridine-carboxylate,
2-trifluoromethylphenyl 2-cyano-1-aziridine-carboxylate,
3-trifluoromethylphenyl 2-cyano-1-aziridine-carboxylate,
4-nitrobenzyl 2-cyano-1-aziridine-carboxylate,
2-hydroxyethyl 2-cyano-1-aziridine-carboxylate, cyclopropyl 2-cyano-1-aziridine-carboxylate
2,2,2-trifluoroethyl 2-cyano-1-aziridine-carboxylate
2-propoxyethyl 2-cyano-1-aziridine-carboxylate benzyl 2-carbamoyl-1-aziridine-carboxylate cyclohexyl 2-carbamoyl 1-aziridine-carboxylate
4-chlorophenyl 2-carbamoyl-1-aziridine-carboxylate isopropyl 1-ethoxycarbonyl-2-aziridine-carboxylate phenyl 2-ethoxycarbonyl-1-aziridine-carboxylate
2,2,2-trichloroethyl 2-isopropylcarbonyl-1-ziridinecarboxylate allyl 2-ethoxycarbonyl-1-aziridine-carboxylate The following examples are given for the purpose of illustrating the present invention:

EXAMPLE 1

Phenyl 2-cyano-1-aziridine-carboxylate

A solution of 12.6 g. phenyl chloroformate in 40 ml. diethyl ether and 40 ml. 2 N aqueous sodium carbonate solution are added simultaneously, at ambient temperature, to 6.8 g. 2-cyanoaziridine in 70 ml. water. The reaction mixture is stirred for 2 hours at ambient temperature, the phases are then separated and the ethereal layer is extracted twice with water, dried and the organic phase evaporated. The evaporation residue is recrystallized from diisopropyl ether. There are obtained 10.3 g. (about 67% of theory) phenyl 2-cyano-1-aziridine-carboxylate;

m.p. 60°-62° C.

The following compounds are obtained in an analogous manner by reacting 2-cyanoaziridine with
1. methyl chloroformate:
   methyl 2-cyano-1-aziridine-carboxylate;
   b.p. 70°-72° C./0.02 mm.Hg
2. 2,2,2-trichloroethyl chloroformate:
   2,2,2-trichloroethyl 2-cyano-1-aziridine-carboxylate;
   b.p. 138°-139° C./0.1 mm.Hg; m.p. 86°-88° C. (recrystallized from diisopropyl ether)
3. allyl chloroformate:
   allyl 2-cyano-1-aziridine-carboxylate;
   b.p. 102°-105° C./0.2 mm.Hg.
4. tert.-butyl chloroformate (used in the form of an ethereal solution):
   tert.-butyl 2-cyano-1-aziridine-carboxylate;
   b.p. 57°-59° C./0.01 mm.Hg.
5. n-pentyl chloroformate (b.p. 98°-100° C./100 mm.Hg):
   n-pentyl 2-cyano-1-aziridine-carboxylate;
   b.p. 93° C./0.01 mm.Hg.
6. cyclohexyl chloroformate (b.p. 47° C./4 mm.Hg):
   cyclohexyl 2-cyano-1-aziridine-carboxylate;
   b.p. 97° C./0.01 mm.Hg.
7. benzyl chloroformate:
   benzyl 2-cyano-1-aziridine-carboxylate;
   b.p. 145°-150° C./0.01 mm.Hg.
8. phenethyl chloroformate (b.p. 120° C./18 mm.Hg):
   phenethyl 2-cyano-1-aziridine-carboxylate;
   b.p. 130° C./0.01 mm.Hg.

EXAMPLE 2

Diethyl 1,2-aziridine-dicarboxylate

A solution of 1.9 g. ethyl chloroformate in 10 ml. benzene is added dropwise at 0° C. to 2 g. ethyl 2-aziridine-carboxylate and 1.7 g. triethylamine in 20 ml. benzene and the reaction mixture is then stirred for 2 hours at ambient temperature, thereafter extracted three times with water and the benzene phase dried and evaporated. The residue obtained is subsequently distilled. There are obtained 2.0 g. (about 62% of theory) diethyl 1,2-aziridine-dicarboxylate; b.p. 94° C./0.2 mm.Hg.

EXAMPLE 3

Phenyl 2-carbamoyl-1-aziridine-carboxylate

A solution of 4.7 g. phenyl chloroformate in 20 ml. diethyl ether and 30 ml. aqueous 2 N sodium carbonate solution are added dropwise and simultaneously to 2.6 g. 2-aziridine-carboxamide in 20 ml. water. The reaction mixture is further stirred for 10 minutes, while cooling with ice. The precipitate obtained is filtered off with suction and well washed with diethyl ether. There are obtained 4.4 g. (about 71% of theory) phenyl 2-carbamoyl-1-aziridine-carboxylate; m.p. 140°-142° C., after recrystallization from toluene.

EXAMPLE 4

Allyl 2-cyano-1-aziridine-carboxylate 3.2 g. Allyl chloroformate in 20 ml. benzene is added dropwise at 0° C. to 2 g. 2-cyanoaziridine in 20 ml. benzene and 3 g. triethylamine. The reaction mixture is further stirred for 2 hours at ambient temperature and the benzene solution is extracted twice with water, dried and the organic phase evaporated. The residue obtained is then distilled. There are obtained 2.9 g.

(about 64.5% of theory) allyl 2-cyano-1-aziridine-carboxylate; b.p. 102°–105° C./0.2 mm.Hg.

In an analogous manner, by reacting 2-cyano-aziridine with ethyl chloroformate, there is obtained ethyl 2-cyano-1-aziridine-carboxylate; b.p. 70°–75°C./0.01 mm.Hg.

EXAMPLE 5

Ethyl 2-carbamoyl-1-aziridine-carboxylate

A solution of 3.25 g. ethyl chloroformate in 20 ml. diethyl ether and 15 ml. aqueous 2 N sodium carbonate solution are added dropwise and simultaneously to 2.6 g. 2-aziridine-carboxamide in 20 ml. water. The reaction mixture is further stirred for 1 hour, while cooling, the phases are then separated, the aqueous phase is evaporated and the residue is boiled with ethanol. The ethanolic solution obtained is filtered and the filtrate evaporated to give a residue which is recrystallized from toluene. There are obtained 2.6 g. (about 56% of theory) ethyl 2-carbamoyl-1-aziridine-carboxylate; m.p. 125°–128° C.

In an analogous manner, by reacting 2-aziridine-carboxamide with methyl chloroformate, there is obtained methyl 2-carbamoyl-1-aziridine-carboxylate which, after recrystallization from toluene, melts at 117°–120° C.

EXAMPLE 6

Preparation of 2-cyano-1-aziridine-carboxamide from phenyl 2-cyano-1-aziridine-carboxylate 1.9 g. Phenyl 2-cyano-1-aziridine-carboxylate are dissolved in 30 ml. diethyl ether and the resulting solution is added dropwise to 20 ml. liquid ammonia. The reaction mixture is stirred for 2 hours at the boiling temperature of ammonia and then allowed to come to ambient temperature overnight. The precipitated 2-cyano-1-aziridine-carboxamide is then filtered off with suction, the yield being 0.85 g. (about 77% of theory); m.p. 74°–76° C.

EXAMPLE 7

Methyl 2-cyano-1-aziridine-carboxylate 14.4 g. Methyl 2-carbamoyl-1-aziridine-carboxylate are added to a solution of 27.5 g. triphenyl phosphine, 10.1 g. triethylamine and 15.4 g. carbon tetrachloride in 300 ml. methylene chloride and the reaction mixture then boiled under reflux for 4 hours. The reaction mixture is subsequently filtered, the filtrate is extracted twice with water and the organic phase is dried and evaporated. The residue obtained is distilled to give 3.4 g. (about 27% of theory) methyl 2-cyano-1-aziridine-carboxylate; b.p. 70°–72° C./0.02 mm.Hg.

EXAMPLE 8

Ethyl 2-carbamoyl-1-aziridine-carboxylate

To 4.67 g. (0.025 mole) diethyl 1,2-aziridine-dicarboxylate in 30 ml. ethanol there is added the equimolar amount of gaseous ammonia dissolved in ethanol and the reaction mixture then left to stand overnight in a refrigerator. The reaction mixture is subsequently evaporated and the desired ethyl 2-carbamoyl-1-aziridine-carboxylate isolated by column chromatography (200 g. silica gel; elution agent acetone/toluene 1:1 v/v). There is obtained 1.4 g. (about 32% of theory) of the ester; m.p. 125°–128° C.

EXAMPLE 9

Preparation of 2-cyano-1-aziridine-carboxamide from ethyl 2-cyano-1-aziridine-carboxylate 4 g. Ethyl 2-cyano-1-aziridine-carboxylate are added to a solution of 0.7 g. gaseous ammonia in 80 ml. water. The reaction mixture is stirred for 4 hours at ambient temperature, then extracted three times with diethyl ether and the aqueous phase thereafter freeze dried. The residue obtained is recrystallized from ethanol, with the addition of diethyl ether. There is obtained 1.05 g. (about 29% of theory) 2-cyano-1-aziridine-carboxamide; m.p. 74°–76° C.

EXAMPLE 10

Ethyl 2-cyano-1-aziridine-carboxylate 0.33 g. Activated zinc dust and some zinc chloride are added to 2.11 g. 2-(N-carbethoxy-N-chloroamino)-3-chloropropionitrile (oily substance; prepared by reacting 2-amino-3-chloropropionitrile hydrochloride (m.p. 153°–155° C.) with ethyl chloroformate in the presence of sodium carbonate and subsequent reaction with tert.-butyl hypochlorite) in 25 ml. ethanol. The reaction mixture is stirred for 12 hours at ambient temperature, filtered with suction and the filtrate evaporated and the residue distilled. There are obtained 0.11 g. (about 8% of theory) ethyl 2-cyano-1-aziridine-carboxylate; b.p. 78°–80° C./0.01 mm.Hg.

EXAMPLE 11

In the manner described in Example 1, there are obtained, by the reaction of 2-cyanoaziridine with
1. isobutyl chloroformate;
    isobutyl 2-cyano-1-aziridine-carboxylate;
    b.p. 108°–110° C./0.1 mm.Hg.
2. cyclopropylmethyl chloroformate (b.p. 45°–46° C./12 mm.Hg):
    cyclopropylmethyl 2-cyano-1-aziridine-carboxylate;
    b.p. 107°–109° C./0.1 mm.Hg.
3. but-2-enyl chloroformate (b.p. 25°–28° C./0.1 mm.Hg):
    but-2-enyl 2-cyano-1-aziridine-carboxylate; oily product.
4. cyclopentyl chloroformate (b.p. 60°–61° C./16 mm.Hg):
    cyclopentyl 2-cyano-1-aziridine-carboxylate; oily product.
5. bornyl chloroformate (b.p. 108°–110° C./12 mm.Hg):
    bornyl 2-cyano-1-aziridine-carboxylate;
    b.p. 153°0 C./0.1 mm.Hg.
6. 2-fluoroethyl chloroformate (b.p. 110°–113° C.):
    2-fluoroethyl 2-cyano-1-aziridine-carboxylate;
    b.p. 120° C./0.1 mm.Hg.
7. 2-chloroethyl chloroformate (b.p. 83°–86° C./40 mm.Hg):
    2-chloroethyl 2-cyano-1-aziridine-carboxylate; oily product.
8. 2-bromoethyl chloroformate:
    2-bromoethyl 2-cyano-1-aziridine-carboxylate; oily product.
9. 2-methoxyethyl chloroformate:
    2-methoxyethyl 2-cyano-1-aziridine-carboxylate;
    b.p. 119°–120° C./0.1 mm.Hg.
10. tetrahydrofurfuryl chloroformate (b.p. 68° C./0.2 mm.Hg):

tetrahydrofurfuryl 2-cyano-1-aziridine-carboxylate; oily product.
11. ethylene glycol 1,2-bis-chloroformate (b.p. 110° C./34 mm.Hg):
   1,2-[bis-(2-cyanoaziridine-1-carbonyloxy)]-ethane; oily product.
12. 2-phenoxyethyl chloroformate (b.p. 97°-99° C./0.1 mm.Hg):
   2-phenoxyethyl 2-cyano-1-aziridine-carboxylate; oily product.
13. 2-phenylthioethyl chloroformate:
   2-phenylthioethyl 2-cyano-1-aziridine-carboxylate; oily product.
14. 1-naphthyl chloroformate (b.p. 86°-90° C./0.1 mm.Hg):
   1-naphthyl 2-cyano-1-aziridine-carboxylate; oily product.
15. 4-methylphenyl chloroformate (b.p. 105°-106° C./30 mm.Hg):
   4-methylphenyl 2-cyano-1-aziridine-carboxylate; m.p. 88°-90° C. (recrystallized from isopropanol).
16. 2,4-dimethylphenyl chloroformate (b.p. 100°-101° C./12 mm.Hg):
   2,4-dimethylphenyl 2-cyano-1-aziridine-carboxylate; m.p. 90°-91° C. (recrystallized from ethanol).
17. 4-sec.-butylphenyl chloroformate (b.p. 122°-123° C./12 mm.Hg):
   4-sec.-butylphenyl 2-cyano-1-aziridine-carboxylate;
   m.p. 74°-75° C. (recrystallized from ligroin).
18. 4-biphenyl chloroformate:
   4-biphenyl 2-cyano-1-aziridine-carboxylate; m.p. 107°-109° C.
19. 4-methoxyphenyl chloroformate (b.p. 115°-117° C./12 mm.Hg):
   4-methoxyphenyl 2-cyano-1-aziridine-carboxylate; m.p. 54°-57° C. (recrystallized from diisopropyl ether).
20. 4-chloro-2-methoxyphenyl chloroformate (b.p. 138°-140° C./20 mm.Hg):
   4-chloro-2-methoxyphenyl 2-cyano-1-aziridine-carboxylate; m.p. 114°-115° C. (recrystallized from isopropanol).
21. 2-fluorophenyl chloroformate (b.p. 68°-70° C./12 mm.Hg):
   2-fluorophenyl 2-cyano-1-aziridine-carboxylate; m.p. 55°-56° C. (recrystallized from isopropanol/water).
22. 4-trifluoromethylphenyl chloroformate (b.p. 82°-84° C./12 mm.Hg):
   4-trifluoromethylphenyl 2-cyano-1-aziridine-carboxylate; m.p. 75°-77° C. (recrystallized from diisopropyl ether).
23. 4-hlorophenyl chloroformate (b.p. 97°-99° C./12 mm.Hg):
   4-chlorophenyl 2-cyano-1-aziridine-carboxylate; m.p. 79°-82° C. (recrystallized from diisopropyl ether).
24. 2,4-dichlorophenyl chloroformate (b.p. 112°-117° C./8 mm.Hg):
   2,4-dichlorophenyl 2-cyano-1-aziridine-carboxylate; m.p. 82°-84° C.
25. 2,4,5-trichlorophenyl chloroformate (m.p. 58°-60° C.):
   2,4,5-trichlorophenyl 2-cyano-1-aziridine-carboxylate; m.p. 100°-103° C. (recystallized from diisopropyl ether).
26. 4-bromophenyl chloroformate (b.p. 111°-113° C./12 mm.Hg):
   4-bromophenyl 2-cyano-1-aziridine-carboxylate; m.p. 96°-100° C. (recrystallized from diisopropyl ether).
27. 3-nitrophenyl chloroformate (b.p. 120°-122° C./0.5 mm.Hg):
   3-nitrophenyl 2-cyano-1-aziridine-carboxylate; m.p. 98°-100° C. (recrystallized from isopropanol).
23. 4-nitrophenyl chloroformate:
   4-nitrophenyl 2-cyano-1-aziridine-carboxylate; m.p. 107°-111° C. (recrystallized from diisopropyl ether).
29. 4-methylthiophenyl chloroformate (b.p. 108° C./0.2 mm.Hg):
   4-methylthiophenyl 2-cyano-1-aziridine-carboxylate;
   m.p. 73°-75° C. (recrystallized from isopropanol).
30. 2-methylsulphonylphenyl chloroformate (m.p. 100°-103° C.):
   2-methylsulphonylphenyl 2-cyano-1-aziridine-carboxylate;
   m.p. 145°-150° C. (recrystallized from isopropanol).
31. 3-formylphenyl chloroformate (b.p. 125° C./0.4 mm.Hg):
   3-formylphenyl 2-cyano-1-aziridine-carboxylate; oily product.
32. 4-acetylphenyl chloroformate (b.p. 121°-123° C./5 mm.Hg):
   4-acetylphenyl 2-cyano-1-aziridine-carboxylate; m.p. 104°-107° C.
33. 4-carbomethoxyphenyl chloroformate (m.p. 47°-50° C.):
   4-carbomethoxyphenyl 2-cyano-1-aziridine-carboxylate;
   m.p. 85°-87° C. (recrystallized from isopropanol).
34. 4-cyanophenyl chloroformate (b.p. 92°-94° C./0.1 mm.Hg):
   4-cyanophenyl 2-cyano-1-aziridine-carboxylate; m.p. 95°-99° C. (recrystallized from ethyl acetate/ligroin).
35. 2-phthalimidoethyl chloroformate (m.p. 75°-77° C.):
   2-phthalimidoethyl 2-cyano-1-aziridine-carboxylate;
   m.p. 160°-163° C. (recrystallized from ethanol).

Compounds which are obtained as oily products were characterised by NMR and mass spectroscopy.

The immuno-stimulant activity of the novel compounds was determined as follows:

Each time 10 female adult Sprague-Dawley rats were kept fasting over night and the following morning blood was taken from the retroorbital venous plexus. After decomposition of the erythrocytes with saponin, the leucocytes were counted by means of a Coulter counter. Subsequently thereto, the compounds to be tested were orally applied to the rats by means of a throat tube at a dosage of 200 mg. per kilo in 5% tylose. Four days after the application, again after keeping the rats fasting overnight, blood was taken from the retroorbital venus plexus by means of a heparinized puncture capillary and the leucocytes were again counted. The averages with standard deviations were calculated for 10 animals each time. As control, 10 adult Sprague-Dawley rats were treated in similar manner except that, instead of the preparation, only 5% Tylose (10 ml per kilo) were applied.

Results:

The following table contains the results of the leucocytosis. The first column indicates the example of the active compound administered, second column contains the leucocyte values prior to the application of the compounds according to the invention, and the third column contains the leucocyte values four days after the application of the compounds. The fourth and fifth columns indicate the control values, i.e., the fourth column the value for the control on day zero and the fifth column the value for the control day +4. The increases in leucocytes resulting from administration of the novel compounds are physiologically significant. Leucocytes Upon Administration 200 mg/kg to Rats per os

TABLE

| Active Compound of Example | Leucocytes in thousands | | Control | |
|---|---|---|---|---|
| | Initially Day 0 | Day 4 | Initially Day 0 | Day 4 |
| 1 | 7.5 | 15.5 | 7.6 | 9.4 |
| 1.1 | 6.0 | 15.8 | 6.8 | 7.9 |
| 1.2 | 7.2 | 13.7 | 7.6 | 9.4 |
| 1.3 | 7.4 | 11.8 | 6.3 | 7.0 |
| 1.4 | 6.0 | 11.2 | 6.3 | 7.0 |
| 1.8 | 5.6 | 10.7 | 6.8 | 7.9 |
| 4.1 | 6.8 | 18.0 | 7.3 | 9.5 |
| 11.10 | 6.2 | 10.6 | 6.2 | 8.2 |
| 11.15 | 6.7 | 12.5 | 6.5 | 7.7 |
| 11.16 | 6.3 | 11.3 | 6.5 | 7.7 |
| 11.19 | 7.2 | 12.5 | 6.4 | 8.2 |
| 11.21 | 6.6 | 12.2 | 6.4 | 8.2 |
| 11.23 | 5.8 | 11.2 | 6.5 | 7.7 |
| 11.25 | 6.0 | 12.3 | 7.0 | 9.2 |
| 11.26 | 7.1 | 13.4 | 6.4 | 8.2 |
| 11.33 | 6.3 | 12.5 | 6.2 | 8.2 |

The present invention also provides pharmaceutical compositions comprising the new compound and/or at least one solid or liquid pharmaceutical diluent or carrier.

For the preparation of pharmaceutical compositions, a 1-aziridine-carboxylic acid ester derivative in accordance with the invention is mixed in known manner with an appropriate pharmaceutical carrier substance and formed, for example, into tablets or dragees or, with the addition of appropriate adjuvants, suspended or dissolved in water or an oil, for example olive oil, and placed in capsules. Since the active material is acid labile, the composition is provided with a coating which only dissolves in the alkaline medium of the intestines or an appropriate carrier material, for example a high molecular weight fatty acid or carboxymethyl-cellulose is mixed therewith. Examples of solid carrier materials include starch, lactose, mannitol, methyl cellulose, talc, highly dispersed silicic acids, high molecular weight fatty acids (for example stearic acid), gelatin, agar-agar, calcium phosphate, magnesium stearate, animal and vegetable fats and solid high molecular weight poylmers (such as polyethylene glycols). Compositions suitable for oral administration can, if desired, contain flavoring and/or sweetening materials.

However, the active material is preferably injected. As injection medium, it is preferred to use water which contains the additives usual in the case of injection solutions, such as stabilizing agents, solubilizing agents and/or weakly alkaline buffers. Additives of this type include, for example, phosphate and carbonate buffers, ethanol, complexforming agents (for example ethylenediamine-tetraacetic acid and the non-toxic salts thereof) and high molecular weight polymers (for example liquid polyethylene oxide) for viscosity regulation.

For treatment of humans the active material may be applied one or more times with each dose containing about 25 to 3000 and preferably 50 to 500 mg of active material.

It will be appreciated that the instant specification and examples are set forth by way of illustration and not limitation, and that various modifications and changes may be made without departing from the spirit and scope of the present invention.

We claim:

1. A 1-aziridine-carboxylic acid ester compound of the formula

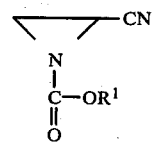

wherein $R^1$ is methyl; propyl; butyl; amyl; a $C_{2-5}$ unsaturated aliphatic hydrocarbon radical; a $C_{1-5}$ aliphatic hydrocarbon radical substituted up to three times by chlorine, bromine, fluorine, $C_{1-5}$ alkoxy, amino, carbamolyoxy, $C_{3-10}$ cycloalkyl, hydroxyl, a phthalimido radical, or a tetrahydrofuryl or tetrahydrothienyl radical, cycloalkyl; or phenyl, naphthyl, benzyl, phenethyl, phenoxyethyl or phenylthioethyl wherein the phenyl or naphthyl moiety is optionally substituted up to 3 times by chlorine, bromine, fluorine, $C_{1-5}$ alkyl, $C_{1-5}$ alkoxy, hydroxyl, amino, nitro, cyano, formyl, acetyl, carbo $C_{1-5}$ alkoxy, $-SCH_3$, phenyl or trifluoromethyl.

2. A compound according to claim 1, wherein such compound is phenyl-2-cyano-1-aziridine-carboxylate of the formula

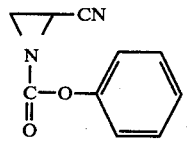

3. A compound according to claim 1, wherein such compound is methyl-2-cyano-1- aziridine-carboxylate of the formula

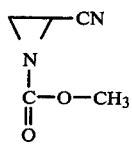

4. A compound according to claim 1, wherein such compound is 2,2,2-trichloroethyl-2-cyano-1-aziridine-carboxylate of the formula

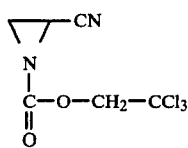

5. A compound according to claim 1, wherein such compound is 2,4,5-trichlorophenyl-2-cyano-1-aziridine-carboxylate of the formula

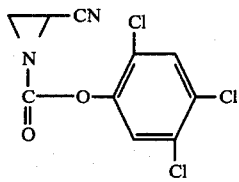

6. A compound according to claim 1, wherein such compound is 4-bromophenyl-2-cyano-1-aziridine-carboxylate of the formula

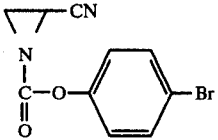

7. A compound according to claim 1, wherein such compound is 4-carbomethoxyphenyl-2-cyano-1-aziridine-carboxylate of the formula

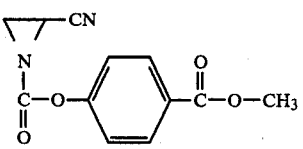

8. A compound according to claim 1, wherein such compound is allyl 2-cyano-1-aziridine-carboxylate of the formula

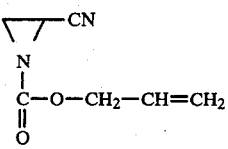

* * * * *